United States Patent [19]

Krisp et al.

[11] 4,217,234

[45] Aug. 12, 1980

[54] DENTURE CLEANSING TABLET AND METHOD OF MANUFACTURING THE SAME

[76] Inventors: Werner Krisp, Heinestrasse 9, 6940 Weinheim; Mira Reuss, Nietzschestrass 4, 6800 Mannheim, both of Fed. Rep. of Germany.

[21] Appl. No.: 878,277

[22] Filed: Feb. 16, 1978

[51] Int. Cl.$^2$ .................. C11D 3/065; C11D 7/18; C11D 17/00
[52] U.S. Cl. ..................... 252/99; 252/102; 252/149; 252/524; 252/527; 252/531; 252/538; 252/539
[58] Field of Search ............... 252/90, 95, 99, 100, 252/134, 135, 527, 539, 102, 149, 524; 424/44, 149

[56] References Cited

U.S. PATENT DOCUMENTS

| | | | |
|---|---|---|---|
| 2,498,344 | 2/1950 | Rider et al. | 252/103 |
| 3,337,466 | 8/1967 | Puetzer et al. | 252/99 |
| 3,372,125 | 3/1968 | Hill | 252/99 |
| 3,607,759 | 9/1971 | Barth | 252/100 |
| 3,821,117 | 6/1974 | Breece et al. | 252/99 |
| 3,962,107 | 6/1976 | Levin et al. | 252/100 |
| 3,997,459 | 12/1976 | Bogie et al. | 252/99 |
| 4,062,793 | 12/1977 | Schodel | 252/99 |
| 4,086,176 | 4/1978 | Walker | 252/143 |

FOREIGN PATENT DOCUMENTS

| | | |
|---|---|---|
| 264015 | 8/1968 | Austria . |
| 275044 | 10/1969 | Austria . |
| 2357720 | 5/1975 | Fed. Rep. of Germany . |
| 962469 | 7/1964 | United Kingdom . |

OTHER PUBLICATIONS

The Condensed Chemical Dictionary, Reinhold Publishing Co., N. Y., Fourth Edition, 1950, pp. 215-216.

*Primary Examiner*—P. E. Willis, Jr.
*Attorney, Agent, or Firm*—George W. Rauchfuss, Jr.; Eugene O. Retter

[57] ABSTRACT

A fast-acting (3-5 min.) denture-cleansing tablet for use in aqueous solutions to automatically clean dentures is comprised of a mixture containing gas-forming materials, organic and inorganic calcium bonding materials, oxidizing materials, surfactant materials, carriers, lubricants and flavoring materials. Fast cleansing action and short decomposition times are obtained by including amidosulfonic acid, ethylene diamine tetraacetic acid, dialkyl thiourea, and a non-ionogenic fluorochemical material in an amount sufficient to achieve a pH in a 1% solution of such formulation in water of 6.3 to 6.5.

12 Claims, No Drawings

DENTURE CLEANSING TABLET AND METHOD OF MANUFACTURING THE SAME

BACKGROUND OF THE INVENTION

1. Field of the Invention

The invention relates to denture-cleansing compositions and somewhat more particularly to denture-cleansing tablets and methods of manufacturing the same.

2. Prior Art

Denture-cleansing compositions for use in aqueous solutions to automatically clean dentures which comprise a mixture containing sodium hydrogen carbonate as a gas-forming agent, sodium polyphosphate as a calcium-bonding agent, additional organic calcium-bonding agents and acid carriers, caroates as oxidizing agents, surfactants in the form of alkyl or alkyl aryl sulfonates, alkyl benzene sulfonates and inert carriers (excipients) and lubricants (releasants) are known.

German Offenlegungsschrift (DOS) No. 2,357,720 discloses a two-layer denture-cleansing tablet wherein at least one of the layers is composed of a mixture containing the foregoing materials so that a formulation for a tablet contains 15 to 25 wt. % of sodium hydrogen carbonate, 8 to 15 wt. % of sodium hexametaphosphate and acid disodium pyrophosphate, at least 15 wt. % of citric acid, 2 to 6 wt. % of an ethylene diamine compound, 1 to 4 wt. % of a polymeric surface-active dye carrier having cleansing properties and a dye material, at least 0.5 wt. % of at least one surfactant, 1 to 4 wt. % of a relatively high molecular weight polyethylene glycol and 0.5 to 1.5 wt. % of peppermint or some other flavoring material so that the pH in a 1% solution of such composition in water is 6.5 to 7.0.

In general, in this known cleansing tablet formulation, ethylene diamine tetraacetate is utilized as a complexing agent for forming chelate-complexes for any metal ions present, the sodium hydrogen carbonate is utilized as a pH-stabilizing gas-forming agent, the sodium hexametaphosphate is utilized as a softening agent and the citric acid as a reducing, antimicrobial agent which also dissolves tartar and other foreign coatings on the teeth of the dentures being cleansed. The ethylene diamine tetraacetate in this formulation also has a softening and demineralizing effect as a result of the chelate formation and also aids in dissolving tartar and other foreign coatings on the dentures. The high molecular weight polyethylene glycol functions as an antimicrobial effervescing agent while the surfactants in general have an emulsifying effect and function to dissolve various foreign coatings on dentures as a result of their surface activity. Sodium pyrophosphate in this formulation functions as a reducing and softening agent and also dissolves various coatings on dentures due to the surface activity thereof. The caroates, i.e., salts of Caro's acid, are oxidizing agents. In the known cleansing tablet formulation, the polymeric dye carrier with surface-activity cleansing property is, preferably, a commercially available sodium salt of polycarboxylic acid (more fully described in the earlier cited DOS No. 2,357,720 at page 17, lines 15-16), which is said to also improve the cleansing action of the overall formulation. The alkyl benzene sulfonate used as a surfactant in this formulation is, for example, sodium dodecyl benzene sulfonate to which fatty acid disodium sulfosucciantes may also be added. The preferred molecular weight of the polyethylene glycol used in the known formulation may range between 4000 and 25,000 but is most preferably about 20,000.

Generally, the foregoing prior art denture-cleansing tablet formulation yields relatively good results. However, in many applications it is desirable to obtain a much shorter cleansing time than the about 10 to 15 minutes required with this prior art formulation. Further, the two-layer tablet structure disclosed by DOS No. 2,357,720 is relatively expensive to manufacture.

It is also known that deposits of calcium compounds on dentures or metal parts thereof or on jaw-regulating apparatuses can be more effectively dissolved or removed by special acid cleansing agents, such as described, for example, in Swiss Patent Specification No. 480,840, which, in a 1% aqueous solution, have a pH of 1.5 to 5. However, a disadvantage of these acid agents is that they inhibit the desired action of the chelate-forming complexing agents required in denture-cleansing formulations since such complexing agents cannot function at a pH below about 6.

SUMMARY OF THE INVENTION

The invention provides an improved denture-cleansing tablet formulation and a method of manufacturing the same whereby the above prior art disadvantages are overcome and a denture-cleansing tablet consisting of a single layer structure is provided and which is extremely rapidly acting and provides reliable cleansing of dentures.

In accordance with the principles of the invention, a denture-cleansing formulation is provided substantially along the lines noted earlier, except that the calcium-bonding organic acid is amidosulfonic acid (sulphamic acid), the ethylene diamine compound is ethylene diamine tetraacetic acid (sometimes referred to as $H_4EDTA$); and includes about 1.5 to 2.5 wt. % of dialkyl thiourea and about 0.2 to 0.5 wt. % of a non-ionogenic fluorochemical substance so that the pH of such tablet formulation in a 1% aqueous solution is 6.3 to 6.5 and such tablet exhibits a total decomposition time of 1 to 2 minutes and a total cleansing time of 3 to 5 minutes.

In a preferred embodiment of the invention, the polymeric dye carrier comprises 1 to 2 wt. % of a commercial sodium salt of polycarboxylic acid (see DOS No. 2,357,720, page 17, lines 15-16, which is incorporated herein by reference), preferably sodium polyacrylate. In a particularly favorable embodiment of the invention, between 1 and 2 wt. % of a crosslinked polyvinyl polypyrrolidone is utilized in the tablet formulation.

An exemplary formulation of a denture-cleansing tablet formulated in accordance with the invention and which yields particularly good results is comprised of about 10 to 12 wt. % of sodium hexametaphosphate; about 18 to 20 wt. % of sodium hydrogen carbonate; about 1.5 to 2.0 wt. % of polyethylene glycol having a molecular weight of about 20,000; 24 to 30 wt. % of amidosulfonic acid; about 20 to 24 wt. % of a caroate; about 5.5 to 7.5 wt. % of an acid disodium pyrophosphate; about 2 to 3 wt. % of ethylene diamine tetraacetic acid; about 0.5 to 2.0 wt. % of a sodium salt of a polycarboxylic acid (see DOS 2,357,720, page 17, lines 15-16, which is specifically incorporated herein by reference), along with a dye additive; about 0.5 to 1.5 wt. % of a flavoring agent, such as peppermint powder; 0.5 to 1.5 wt. % of sodium dodecyl benzene sulfonate; about 0.3 to 1.0 wt. % of lauryl polyglycol ether sulfosuccinate; about 0.2 to 0.4 wt. % of a non-ionogenic fluorochemical substance; about 0.8 to 1.1 wt. % of sodium benzoate; about 1.5 to 2.0 wt. % of a dialkyl thiourea; about 1.5 to 2.0 wt. % of polyvinyl polypyrrolidone; about 0.5 to 1.5 wt. % of disodium sulfosuccinate; and about 0.8 to 1.2 wt. % of an alkyl aryl sulfonate.

In accordance with the principles of the invention, the denture-cleansing formulation of the invention is manufactured into a cleansing tablet by first admixing the proper amounts of sodium hydrogen carbonate, sodium hexametaphosphate, polyethylene glycol and about 30 to 50 wt. % of the total amount of the amidosulfonic acid; forming a granulate product of the resulting mixture; mixing the resulting granulate product with the remaining ingredients of the formulation and manufacturing a cleansing tablet from the so-attained mixture.

DESCRIPTION OF THE PREFERRED EMBODIMENTS

The invention provides an improved denture-cleansing tablet formulation and a method of manufacturing a cleansing tablet from such formulation and which is characterized by a relatively fast decomposition time and a relatively fast cleansing time.

In contrast to the prior art denture-cleansing tablets (of course, the compositions of the invention may, if desired, also be utilized as a pulverized cleansing agent, in which case molding and lubricating agents used for tablet manufacture can be omitted), which are very alkaline, neutral or weakly acidic (such as the cleansing tablet formulation of DOS No. 2,357,720), the pH of denture-cleansing tablets produced in accordance with the principles of the invention is precisely adjusted so as to range between 6.3 to 6.5, with a pH fluctuation of not more than ±0.3.

With denture-cleansing tablets of the invention, a user is no longer limited to cleaning his dentures once a day to remove a daily accumulation of deposits (food residues, saliva, tartar, etc.) and because the denture-cleansing formulation of the invention has a previously unattainable decomposition time of 1 to 2 minutes and a total cleansing time of only 3 to 5 minutes, a user may conveniently cleanse his dentures as often as he desires and more than once a day.

An important feature of the invention is that amidosulfonic acid is used in combination with a dialkyl thiourea compound which is an anti-corrosive agent and acts as an inhibitor for the amidosulfonic acid and reliably prevents damage to the denture material or the metal components thereof. A suitable dialkyl thiourea compound (quarternary heterocyclic alkyl aryl compound, a condensation product of aldehydes and amines) is commercially available under the registered trademark "LITHSOLVENT" (for example, available from Keller & Bohacek KG, Dusseldorf, Germany). The anti-corrosion agent or inhibitor appears to act synergistically with the sodium benzoate (a known disinfectant) provided within the denture-cleansing formulation of the invention and this results in a further synergistic effect with the active oxygen (released from the caroates within the formulation) since the inhibitor is also an anti-oxidizing agent. In addition, there is a synergism between the anti-corrosion agent (dialkyl thiourea) and the amidosulfonic acid, which prevents the peroxides within the formulation from decomposing during storage of the denture-cleansing tablets.

A preferred form of sodium hexametaphosphate utilized in the denture-cleansing tablet formulations of the invention is a so-called instant-acting sodium hexametaphosphate which is commercially available under the registered trademark "BUDIT 8 H".

Because the denture-cleansing tablet formulation of the invention utilizes pulverized ethylene diamine tetraacetic acid which has a pH of 2.5 to 3 in a saturated aqueous solution, the amount of this chelate-forming complexing agent is considerably less than when a conventional form of ethylene diamine tetraacetate is utilized. A pulverized ethylene diamine tetraacetic acid ($H_4EDTA$) of the type useful in the practice of the invention is commercially available under the registered trademark "VERSENE ACID" (for example, available from the Dow Chemical Company).

In accordance with the principles of the invention, surfactants are combined with a non-ionogenic fluorochemical substance and this results in providing cleansing solutions (i.e., after decomposition of a denture tablet in water) which has an extremely low surface tension of about 25 to 26 dynes/cm. As a result of such low surface tension, the wetting power or emulsification action of the resultant cleansing solution is greatly increased, resulting in a very short cleansing time, which is a characteristic of the denture-cleansing tablets of the invention. Preferred surfactants utilized in the denture-cleansing tablet formulations of the invention are surfactants such as sodium dodecyl benzene sulfonate and lauryl polyglycol ether sulfosuccinate, respectively commercially available under the registered trademarks "STEINAPOL NKS 100" and "REWO-DERM S 1333" (for example, from Rewo Chemische Fabrik GmbH, Steinau, Germany). These surfactants yield a relatively permanent, creamy, stiff foam and the surface tension in a 0.1% aqueous solution of "STEINAPOL NKS 100" is about 25 dynes/cm whereas the surface tension of an identical aqueous solution of "REWO-DERM S 1333" is about 30 to 35 dynes/cm. However, the surface tension of the overall cleansing solution obtained by dissolving a denture-cleansing tablet of the invention is reduced to about 25 to 26 dynes/cm by adding the non-ionogenic fluorochemical substance into such formulation. Suitable non-ionogenic fluorochemical substances are commercially available under the registered trademark "MONFLOR 51" or "MONFLOR 52" (for example, from ICI), and are added in a concentration of about 0.2 to 0.5 wt. % to the denture-cleansing formulation of the invention. This non-ionogenic fluorochemical substance materially increases the wetting power and penetration power of the surfactants present within the denture-cleansing tablet formulation. Monflor 51 is a non-ionogenic compound of the formula $C_8F_{15}O(CH_2CH_2O)nCH_3$ wherein $C_8F_{15}$ is the residue of the tetremer of tetrafluoro ethylene and n has an average value of 8 and Monflor 52 is a non-ionogenic compound of the formula $C_8F_{15}O(CH_2CH_2O)nC_8F_{15}$ wherein $C_8F_{15}$ is the residue of the tetramer of tetrafluoro ethylene and n has an average value of 23.

The denture-cleansing tablet formulation of the invention provides, for the first time, a very rapidly acting cleansing agent in a denture-cleansing solution having a surface tension of only 25 to 26 dynes/cm whereas the average surface tension of other cleansing solution is about 35 to 90 dynes/cm.

The molding and other auxiliary materials used with the denture-cleansing tablet formulation of the invention may comprise the typical molding and other auxiliary agents used with prior art denture-cleansing formulations, such as set forth in the earlier noted DOS No. 2,357,720, for example, fatty acid esters of sugar commercially available under the registered trademark "WASAG 7" or "WASAG 15" (these products are available under the registered trademark "SUCRAPAN" in Switzerland, Austria and East Europe). Alternatively, the molding and lubricating agents may be materials available under the registered trademarks "LUVISKOL V64", "AERSOSIL", "TAMOL", "AWYCEL" (methyl celluloses) or "WAXY MAIS" (starch). In general, the molding and lubricating agents comprise native starches, sugar starches and derivatives thereof, such as glucose, anhydrous dextrose, polyethylene glycol and microcrystalline cellulose.

With the foregoing general discussion in mind, there is now presented a detailed example which will illustrate to those skilled in the art the manner in which this invention is carried out. However, this example is not to be construed as limiting the scope of the invention in any way.

EXAMPLE

Denture-cleansing tablets in accordance with the principles of the invention were manufactured as follows:

10.55 Parts by weight of a calcium-bonding agent (commercially available under the registered trademark "BUDIT 8H"), 10.85 parts by weight of amidosulfonic acid (sulphamic acid), 19.00 parts by weight of sodium hydrogen carbonate and 1.81 parts by weight of polyethylene glycol having a molecular weight of about 20,000 were obtained and introduced through a conventional hopper and elevator into a mixing heater. The heater was operationally coupled to a GLATT granulator. The materials within the mixed heater were then heated in an air stream having an average temperature of about 100° to 115° C. and the feed air aperture of the apparatus was adjusted to stage 5–6 while the outlet air aperture was adjusted to stage 2–3. In this manner, the ingredients within this apparatus were heated, with continuous agitation to a temperature of about 60° to 65° C. and maintained at such temperature for about 10 minutes so that a granulated product was obtained. At 60° to 65° C., the polyethylene glycol melts and during the processing time of about 10 minutes produces a granulated product comprised of the admixture of the ingredients.

Next, the air feed and air discharge apertures were adjusted as before and the granulated product was cooled to about 25° C. by passing a stream of cooling air having an average temperature of 6° to 10° C. through the granulated product.

In an alternative procedure, the mixing of the ingredients may be done in a vacuum dryer, such as a tumbling or double-cone dryer operating at a reduced pressure of less than about 80 Torr and preferably at about 50 to 60 Torr and at a temperature of less than about 45° C. and preferably at a temperature of about 32° to 38° C.

In either event, the cooled granulated product was placed in air and moisture-impervious containers, i.e., polyethylene bags or the like, and regular samples thereof taken to check that the maximum moisture content is at least less than 0.5% and preferably less than 0.25%.

Next, 42.21 parts by weight of the above-produced granular product was mixed in a manner described in more detail in the earlier-noted DOS No. 2,357,720 (which, as noted earlier, is incorporated in its entirety herein by reference), with the remaining ingredients of the tablet, i.e., in the present exemplary embodiment, with 22.60 parts by weight of caroate, 6.23 parts by weight of disodium pyrophosphate, 2.26 parts by weight of ethylene diamine tetraacetic acid (VERSENE ACID), 1.18 parts by weight of a commercially available sodium salt of a polycarboxylic acid (see DOS No. 2,357,720, page 17, lines 15–16 for a more complete identification), along with a dye additive, 1.00 parts by weight of peppermint powder, 0.81 parts by weight of sodium dodecylbenzene sulfonate (the earlier noted STEINARYL NKS 100, commercially available from Rewo Chemische Fabrik GmbH), 0.54 parts by weight of lauryl polyglycol ether sulfosuccinate (the earlier noted REWO-DERM S 1333 commercially available from Rewo Chemische Fabrik GmbH), 0.30 parts by weight of a non-ionogenic fluorochemical substance (the earlier noted "MONFLOR 51" commercially available from ICI), 0.90 parts by weight of sodium benzoate, 1.81 parts by weight of dialkyl thiourea (the earlier noted "LITHSOLVENT", commercially available from Keller and Bohacek KG), 1.81 parts by weight of polyvinyl polypyrrolidone (commercially available under the registered trademark "PLASDONE XL" from GAF (Germany) GmbH), 1.00 parts by weight of disodium sulfosuccinate (the earlier noted "WASANG 7"), 1.00 parts by weight of an alkyl aryl sulfonate (the earlier noted "WASANG 15"), and 16.27 parts by weight of amidosulfonic acid (sulphamic acid). After thoroughly mixing, drying and screening, the resultant mixture was molded into a singlelayer denture-cleansing tablet in a conventional manner.

The various features of the invention described in the above description and in the following claims may be important, either singly or in any combination, for bringing about the various embodiments of the invention. Accordingly, as is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

We claim as our invention:

1. A denture-cleansing tablet of single layer structure for use in an aqueous solution for cleansing dentures wherein the tablet is formed from a formulation containing about 15 to 25 wt. % of sodium hydrogen carbonate, about 10 to 12 wt. % of sodium hexametaphosphate, about 5.5 to 7.5 wt. % of acid disodium pyrophosphate, about 20 to 24 wt. % of a salt of Caro's Acid, about 15 to 30 wt. % of amidosulfonic acid, about 2 to 6 wt. % of ethylene diamine tetraacetic acid, about 1 to 4 wt. % of a polyethylene glycol having a molecular weight of about 4,000 to 20,000, about 0.5 to 2 wt. % of a sodium polyacrylate which is a polymeric surface-active dye carrier having cleansing properties, at least about 0.5 wt. % of at least one surfactant, about 0.8 to 1.1 wt. % of sodium benzoate, about 1.5 to 2.5 wt. % of a dialkyl thiourea and about 0.2 to 0.5 wt. % of a nonionogenic fluorochemical substance selected from the group consisting of a compound of the formula $C_8F_{15}O(CH_2CH_2O)nCH_3$ wherein $C_8F_{15}$ is the residue of the tetramer of tetrafluoro ethylene and n has an average value of 8 and a compound of the formula $C_8F_{15}O(CH_2CH_2O)nC_8F_{15}$ wherein $C_8F_{15}$ is the residue of the tetramer of tetrafluoro ethylene and n has an average value of 23, whereby the pH in a 1% solution of such tablet in water is 6.3 to 6.5, said denture tablet being characterized by a total decomposition time of about 1 to 2 minutes and a total denture-cleansing time of about 3 to 5 minutes and said denture-cleansing solution formed on dissolution of the tablet having a surface tension of about 25 to 26 dynes/cm.

2. A denture-cleansing tablet as defined in claim 1 wherein said sodium acrylate is present in an amount of about 1 to 2 wt. %.

3. A denture-cleansing tablet as defined in claim 1 wherein there is also present in the tablet about 1 to 2 wt. % of a cross-linked polyvinyl pyrrolidone.

4. A denture-cleansing tablet as defined in claim 1 wherein there is also present in the tablet a flavoring agent in an amount of about 0.5 to 1.5 wt. %.

5. A denture-cleansing tablet as defined in claim 1 wherein the tablet contains a formulation which consists essentially of about 10 to 12 wt. % of sodium hexametaphosphate; about 18 to 20 wt. % of sodium hydrogen carbonate; about 1.5 to 2.0 wt. % of polyethylene glycol having a molecular weight of about 20,000; about 24 to 30 wt. % of amidosulfonic acid; about 20 to 24 wt. % of a salt of Caro's acid; about 5.5 to 7.5 wt. % of acid disodium pyrophosphate; about 2 to 3 wt. % of ethylene diamine tetraacetic acid; about 0.5 to 2.0 wt. % of a sodium polyacrylate; about 0.5 to 1.5 wt. % of peppermint powder; about 0.5 to 1.5 wt. % of sodium dodecyl benzene sulfonate; about 0.3 to 1.0 wt. % of lauryl polyglycol ether sulfosuccinate; about 0.2 to 0.4 wt. % of a nonionogenic fluorochemical substance; about 0.8 to 1.1 wt. % of sodium benzoate; about 1.5 to 2.0 wt. % of a dialkyl thiourea; about 1.5 to 2 wt. % of a cross-linked polyvinyl polypyrrolidone; and about 0.5 to 1.5 wt. % of disodium sulfosuccinate.

6. A method of producing a denture-cleansing tablet from the improved formulation as defined in claim 1 wherein the stated amounts of sodium hydrogen carbonate, sodium hexametaphosphate, polyethylene glycol and 30 to 50 wt. % of the total stated amount of aminosulfonic acid are admixed and formed into a granulated product and then the remaining ingredients of the formulation defined in claim 1 are admixed with said granulated product and a denture-cleansing tablet is formed from the resultant mixture.

7. A method as defined in claim 6 wherein the ingredients for producing said granulated product are fed into a granulator, heated therein to a temperature of about 60° to 65° C., agitated at such temperature for about 10 minutes to form the granulated product and then cooled to about 25° C.

8. A method as defined in claim 7 wherein the ingredients for producing said granulated product are heated in a stream of heating air heated at about 100° to 115° C. and the so-formed granulated product is cooled in a stream of cooling air cooled to a temperature of about 6° to 10° C.

9. A method as defined in claim 6 wherein the mixing is done in a vacuum drier at a pressure less than about 80 Torr and at a temperature less than about 45° C.

10. A method as defined in claim 9 wherein the mixing is done at a pressure in the range of about 50 to 60 Torr and at a temperature in the range of about 32° to 38° C.

11. A method as defined in claim 9 wherein the mixture is further processed until a residual moisture of less than about 0.5% remains within the so-produced mixture.

12. A method as defined in claim 11 wherein the mixture is further processed until a residual moisture of less than about 0.25% remains within the so-produced mixture.

* * * * *